United States Patent [19]
Sotiropoulos et al.

[11] Patent Number: 5,642,287
[45] Date of Patent: Jun. 24, 1997

[54] SCULPTURING DEVICE FOR LASER BEAMS

[76] Inventors: Nicholas Sotiropoulos, 3 John Meyers Cir., Glen Mills, Pa. 19342; Gregory Berlin, 450 Timberline Trail, West Chester, Pa. 19382

[21] Appl. No.: 397,410

[22] Filed: Mar. 2, 1995

[51] Int. Cl.⁶ .................. G06F 19/00; G06G 7/64; G06G 7/66
[52] U.S. Cl. .................. 364/474.08; 606/5; 606/6
[58] Field of Search .................. 606/4, 5, 6, 10, 606/11, 12; 364/474.08

[56] References Cited

U.S. PATENT DOCUMENTS

| | | | |
|---|---|---|---|
| 4,911,711 | 3/1990 | Telfair et al. | 606/11 |
| 5,108,388 | 4/1992 | Trokel | 606/5 |
| 5,163,934 | 11/1992 | Munnerlyn | 606/5 |
| 5,188,631 | 2/1993 | L'Esperance | 606/5 |
| 5,195,163 | 3/1993 | Burns et al. | 385/132 |
| 5,207,668 | 5/1993 | L'Esperance | 606/5 |
| 5,219,343 | 6/1993 | L'Esperance | 606/5 |
| 5,219,344 | 6/1993 | Yoder, Jr. | 606/5 |
| 5,312,320 | 5/1994 | L'Esperance | 606/5 |
| 5,356,409 | 10/1994 | Nizzola | 606/4 |
| 5,411,501 | 5/1995 | Klopotek | 606/5 |
| 5,445,633 | 8/1995 | Nakamura et al. | 606/4 |
| 5,461,212 | 10/1995 | Seiler et al. | 606/5 |
| 5,470,329 | 11/1995 | Sumiya | 606/5 |
| 5,549,597 | 8/1996 | Shimmick | 606/5 |

*Primary Examiner*—Paul P. Gordon
*Assistant Examiner*—Robert J. Dolan
*Attorney, Agent, or Firm*—Synnestvedt & Lechner

[57] ABSTRACT

A system and device for sculpturing a laser beam along a laser axis to a target upon command using a device between the laser source and the target. The device includes an adjustable iris aperture perpendicular to the axis. At least one door is aligned to limit the laser beam path. A controller adjusts the aperture and the door to sculpture the laser beam in a predetermined pattern. The controller also controls the laser to direct a laser beam on a target in the predetermined pattern which may be pulsed, the duration and intensity of the pulses being controlled by the controller. An encoders locates the iris and the door with respect to the axis for comparison of the positions with the predetermined pattern. The device is rotatable in clockwise and counterclockwise directions by at least 180 degrees. The doors preferably includes a pair of parallel, diametrically opposed door sections, one section being on each side of the axis that may be operated independently so as to permit movement of each section without the other section or the sections may move symmetrically and simultaneously about the axis. A computer is preferably used to control the positions of the iris and the door means with respect to the axis for comparison with the predetermined pattern. In the preferred embodiment, the target is the human eye and the predetermined pattern is intended to shape the eye to treat it for astigmatism, myopia, or hyperopia.

20 Claims, 7 Drawing Sheets

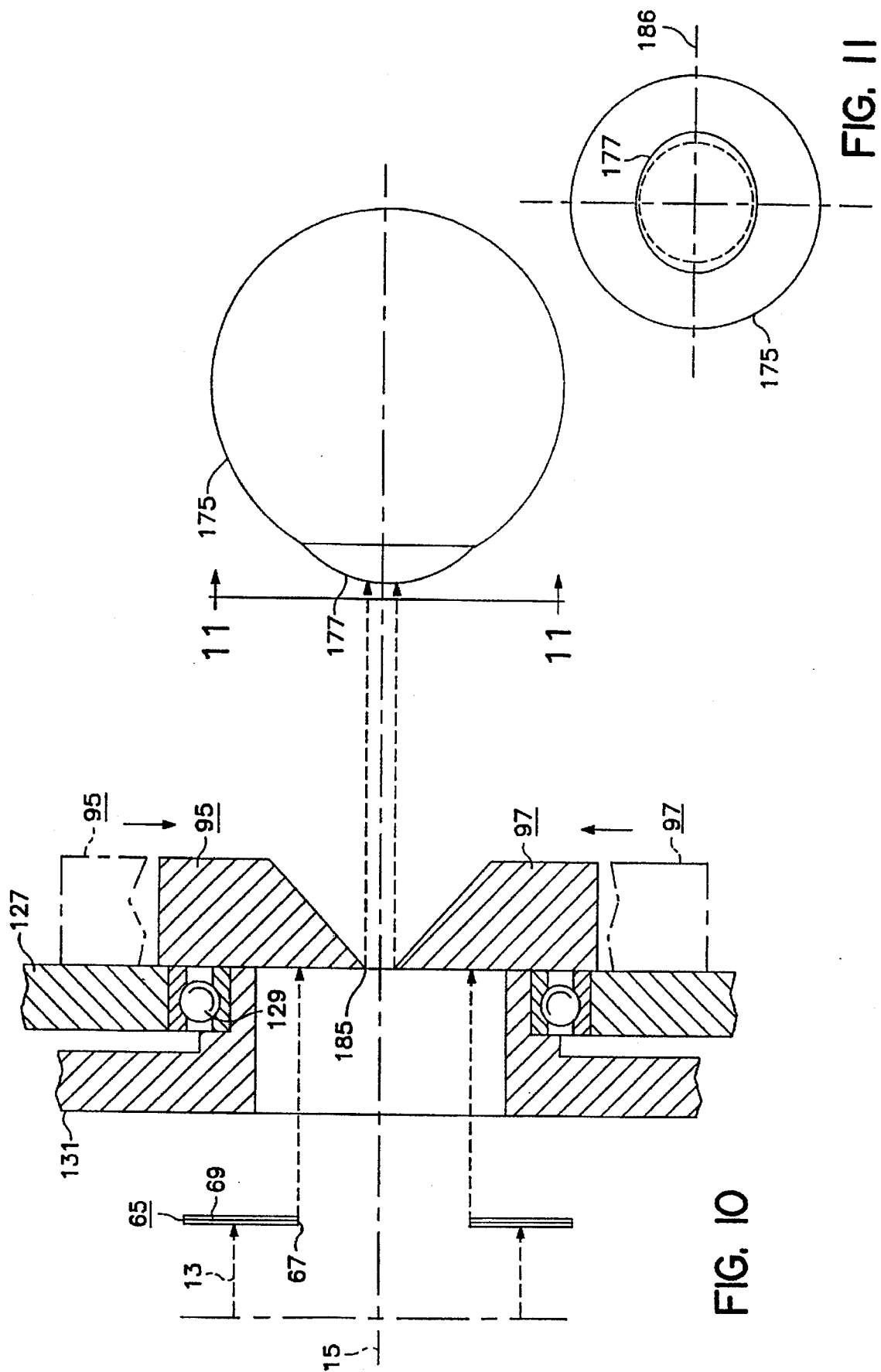

SCULPTURING DEVICE FOR LASER BEAMS

FIELD OF THE INVENTION

The present invention relates to a system and device for sculpturing a laser beam along a laser axis to a target. More particularly the invention relates to a device located between the laser source and the target which is capable of blocking a portion of the laser beam in accordance with a predetermined pattern wherein the portion of the laser beam reaching the target may be varied.

BACKGROUND OF THE INVENTION

The use of lasers to alter the surface of objects is becoming more important as it becomes apparent that lasers may be precisely focused and the amount of energy transferred to the target can be closely controlled. Lasers have been used in eye surgery, for example, to treat the retina of diabetic persons. Lasers have also been used by doctors for other precise and delicate eye surgery.

In all of the prior art eye surgery procedures, as well as in other efforts to use laser beam pulses to act on or burn away tissue or other matter, a great concern arises about the ability to control the size and intensity of the beam. In addition, when multiple treatment pulses are intended, precise location of the beam is desirable.

Until recently, it has not been possible to provide a predetermined pattern of treatment where the intensity and duration of the laser pulse is controlled while simultaneously controlling the shape of the laser pulse and the location where the pulse strikes the target. It has been found that the cornea of the eye may be shaped or otherwise treated with a laser beam pulse in a plurality of locations on the eye to achieve a desired result. Until now, however, it has not been possible to automatically control the size and location of the beam. It has recently been discovered that predetermined control of the laser beam pulse may be accomplished by passing the laser beam through an iris that is centered on the axis of the laser beam. By controlling the size of the iris opening and simultaneously controlling the amount of laser energy passing through the iris aperture, the surface of the eye can be changed to correct for myopia or near sightedness. However, such a procedure has not found acceptance due to the limitations in beam sculpturing that an aperture of this type provides. In addition, the use of an iris only produces a round alteration in laser beam shape, and is therefor not useful for treatment of astigmatism, hyperopia, irregular shapes and even repair of over corrected or inaccurate corrections for myopia.

Accordingly, it is an object of the present invention to provide a system for sculpturing the shape of a laser beam to change the shape of the beam that impacts its intended target.

Another object of this invention is to provide a device which is useful in sculpturing laser beams into shapes that are not perfectly round.

Yet another object of the present invention is to provide a device capable of shaping a laser beam to permit treatment of astigmatism, hyperopia, irregular shapes and even repair of over corrected or inaccurate corrections for myopia.

Other objects will appear hereinafter.

SUMMARY OF THE INVENTION

It has now been discovered that the above and other objects of the present invention may be accomplished in the following manner. Specifically, the present invention provides a system and device for sculpturing a laser beam along a laser axis to a target upon command using a device between the laser source and the target.

The system includes a laser source for directing a laser beam along a laser axis and a target for receiving the laser beam. The device of this invention is located in the laser beam path between the laser source and the target such that the device is aligned to obstruct a portion of the laser beam when it travels on its axis.

In the preferred embodiment, the target is the human eye and more particularly the cornea of a human eye. The predetermined pattern is intended to shape the cornea as the laser contacts it in controlled pulses at predetermined locations on the cornea, preferably to treat astigmatism, myopia, or hyperopia.

The device employed herein includes a housing and frame on which the components that intersect the laser beam along its axis are mounted. Control of the device may be accomplished manually but it is preferred that the various components be controlled by a computer into which the desired data has been entered. A keyboard and video monitor are also used in the system to input data and to observe displays of various treatments being performed.

The device includes an adjustable iris defining an aperture that is aligned perpendicularly with the axis of the laser beam for adjustable movement of the aperture about the axis. The iris is controlled by a control unit receiving instructions from the program of the computer to enlarge or shrink the aperture as planned. The size of the iris aperture is varied by a gear and electric motor assembly that permits accurate adjustment of the aperture dimension to within the needed tolerances.

Also included is a door means that includes at least one door movable in the plane perpendicular to the laser axis so as to further obstruct a portion of the laser beam that would otherwise pass through the iris. Preferably, the door means includes a pair of parallel, diametrically opposed door sections, one section being on each side of the axis. In one embodiment, the door means operates the pair of door sections symmetrically about the axis, preferably such that the symmetrical movement of the pair of door sections is simultaneous.

In the preferred embodiment, the door means operates the pair of door sections independently so as to permit movement of one section without regard to movement of the other section. This independent movement and control allows for substantially more flexibility in designing the predetermined pattern of the laser beam. The door means preferably includes a motor for moving the door sections through gears that allow precise movement that is repeatable with respect to a fixed point in space such as the axis of the laser beam to provide maximum control and effectiveness of the present invention. In the preferred embodiment, each of two door sections are operated by a separate motor.

The control unit is also adapted to rotate the device about the laser axis so that the door sections are capable of intercepting any portion of the laser beam as desired. To accomplish this goal, a portion of the device is adapted to be rotated in both the clockwise and counterclockwise directions so as to provide a full circle of laser beam interception or control.

BRIEF DESCRIPTION OF THE DRAWINGS

For a more complete understanding of the invention, reference is hereby made to the drawings, in which:

FIG. 10 is a is view similar to FIGS. 8 and 9 for astigmatism.

FIG. 11 is a front view, at reduced scale, showing the major axis of an elliptical shaped cornea.

DETAILED DESCRIPTION OF THE PREFERRED EMBODIMENT

Figure 1:
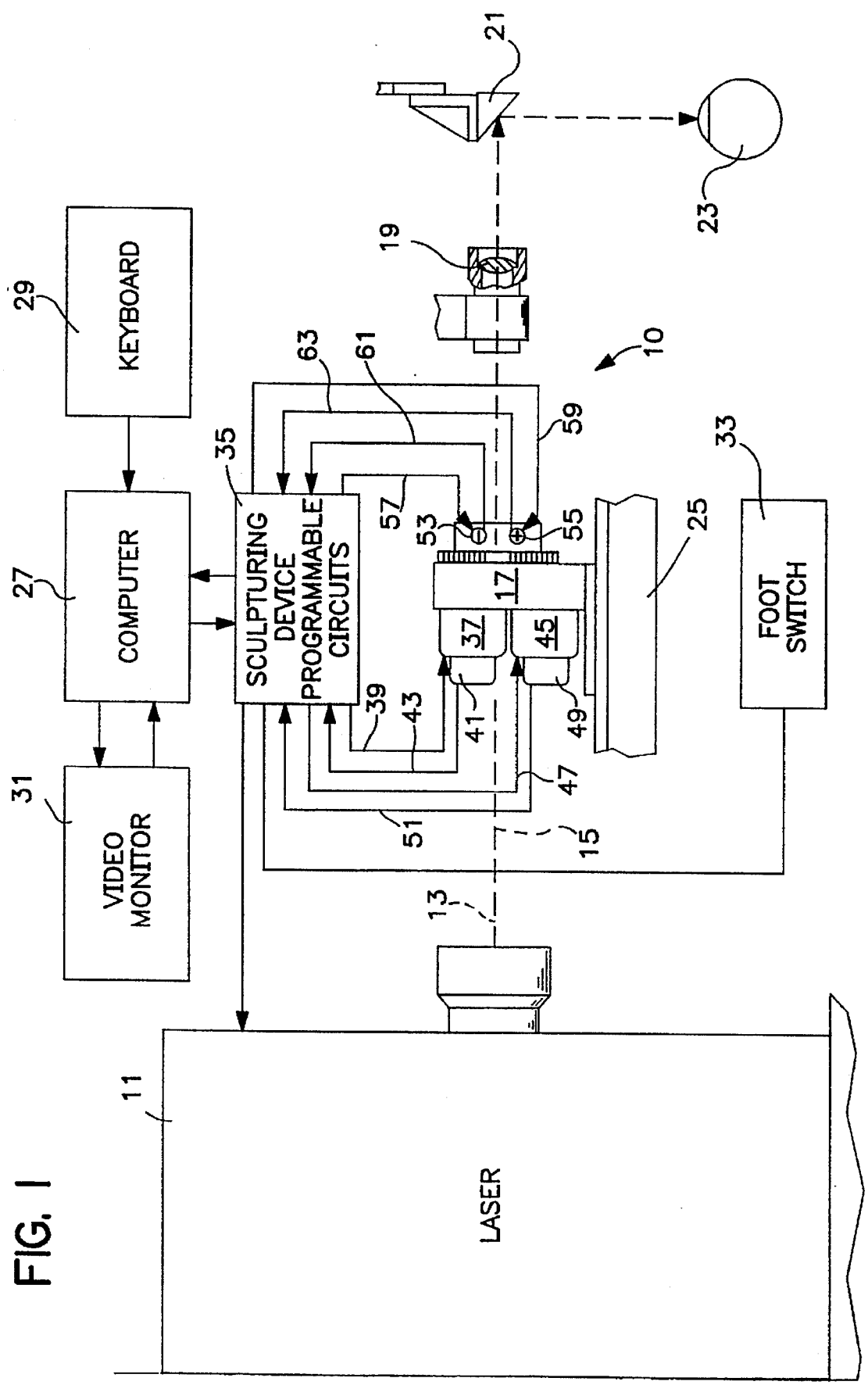
FIG. 1 is a schematic view illustrating the environment and operating components for the sculpturing device of this invention as used in an eye corrective surgical procedure.

As shown in the drawings, a system for sculpturing a laser beam has been developed for control of the laser beam as it acts on the target for which it is intended. The system, generally at 10, includes a laser source 11 directing a laser beam source 13 along an axis 15 through the device of this invention, generally at 17, in which the laser beam is sculptured as described herein. The sculptured beam then passes through a focusing lens assembly 19, is directed by mirror 21, and reaches a target such as eye 23. Focusing lens assembly 19 and mirror 21 are used to align the laser beam properly with respect to the target once the system has been mounted on an appropriate table 25.

The device 17 is controlled by a computer 27 that has a circuit board installed within a computer, such as an IBM PC or an IBM compatible computer. The computer is programmed via keyboard 29 to provide a predetermined pattern of action by the laser, such as, for example, the laser pattern and number of laser pulses for a corneal surgery treatment to correct astigmatism, myopia, or hyperopia. The video monitor 31 allows the operator to review measured or programmed data and to observe displays of various treatments being performed.

The computer program provide instructions to the device 17 to operate four axes of motion. The laser beam is sculptured by passing the beam through the device 17 such that an iris aperture and preferably two doors intersect the beam in a predetermined pattern.

Foot activated switch 33 permits the operator to send activation signals to the system while retaining control over the patient by allowing the operator to position or adjust the target, such as the cornea of a human eye. With the pulsed laser beam, the target is sculptured each time according to the predetermined program, either from the computer software or from direct input from an operator. Note also that when the foot activated switch 33 is used, the operator is also free to use the keyboard 29 at any time. The system of this invention is capable of automated operation with the entire treatment regimen being programmed into the computer so that all that is needed is to position the patient and begin the operation. Alternatively, a doctor may choose to manually input each succeeding pulse or group of pulses of the laser depending upon the results of the preceding pulse or group of pulses.

Turning now to the device shown generally at 17 in FIG. 1, it can be seen that wires connect the device to the control means via computer 27 and circuit board 35 to control a first motor 37 via wire 39 and receive feedback from first encoder 41 via wire 43. Similarly second motor 45 receives input from wire 47 and second encoder 49 provides the needed feedback to computer 27 via wire 51. First and second motors 37 and 45 are mounted on what is described as the front of device 17, where the laser axis 15 enters the sculpturing device. On the back side of device 17 are a pair of motors 53 and 55, shown in FIGS. 2 and 3, that are controlled by input wires 57 and 59 respectively and provide feedback via wires 61 and 63 respectively.

Figure 5:
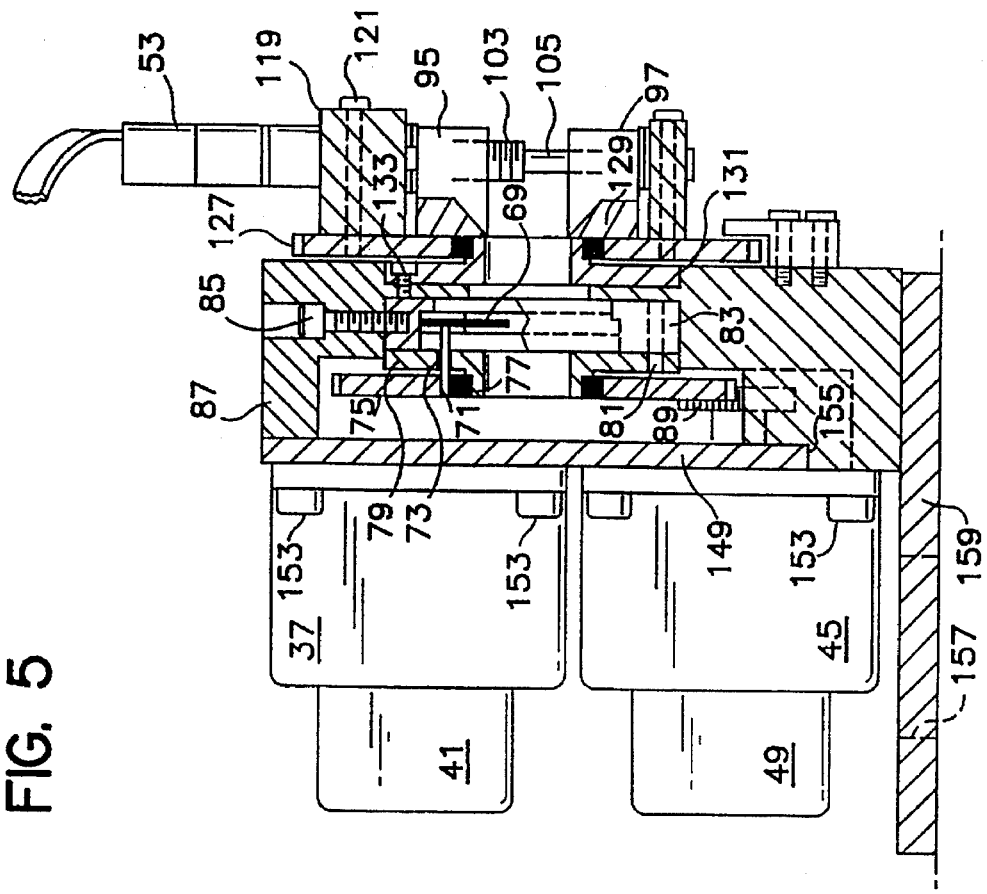
FIG. 5 is a sectional elevational view taken along the line 5,5 of FIG. 4, showing still more details of the iris activating mechanism and the mounting of the adjustable door and slot mechanism.
Figure 4:
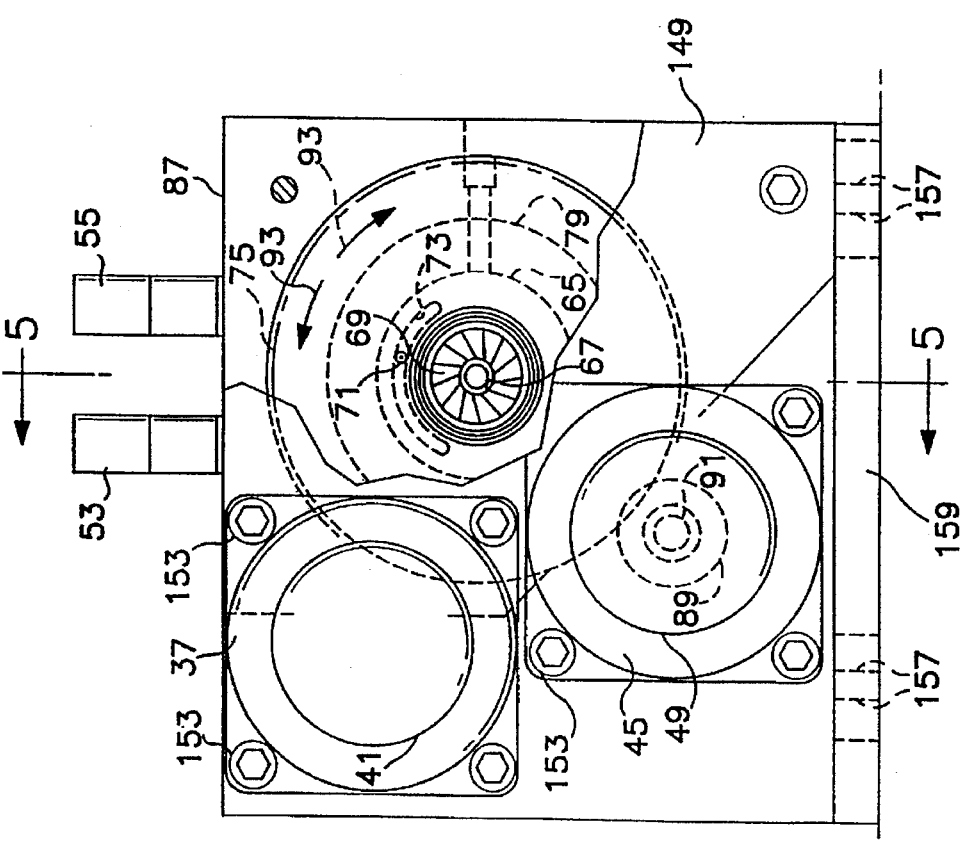
FIG. 4 is a front or left hand elevational view of FIG. 2 with a portion of a cover plate broken away to show certain details of the iris activating mechanism.

The sculpturing device 17 includes an iris 65 shown in FIG. 4 with an aperture 67 that changes in size as the iris diaphragm 69 is changed. Diaphragm 69 is controlled by pin 71 mounted in ring gear 75. Clockwise movement of ring gear 75 opens aperture 67 while counterclockwise movement of ring gear 75 closes diaphragm 69 and therefore aperture 67. FIG. 5 illustrates how ring gear 75 is mounted by bearings 77 on flange 79, with iris 65 also being mounted on flange 79. Flange 79 is pinned to iris retaining ring 83 by pin 81, with iris 65 contained inside retaining ring 83. Large centrally located machine screw 85 locks retaining ring 83 into vertically upstanding housing block 87 also shown in FIG. 5, is the pin 71 extending through arcuate slot 73 in flange 79 to iris 65. The iris actuating ring gear 75 is driven, upon command from the control board as previously described, by second or iris motor 45, which drives spur gear 89 on shaft 91 of motor 45. The movement of the iris diaphragm 69 is the first axis of motion for the present invention, illustrated by arrows 93 in FIG. 4.

Figure 2:
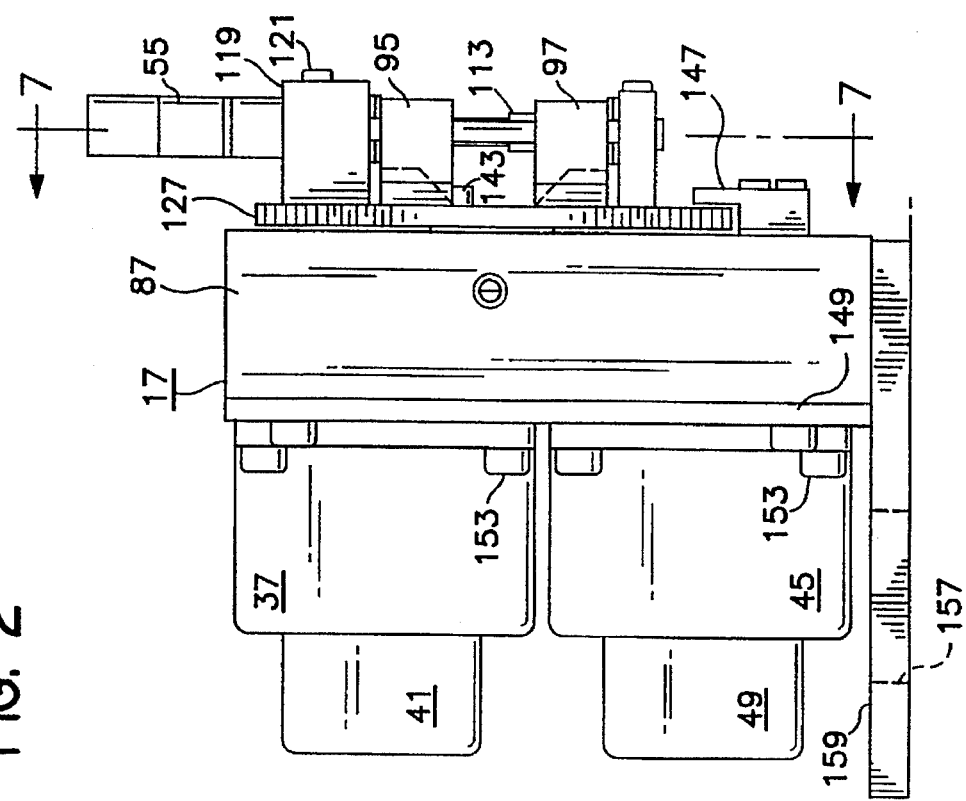
FIG. 2 is an enlarged, side elevational view of the device shown in FIG. 1.
Figure 7:
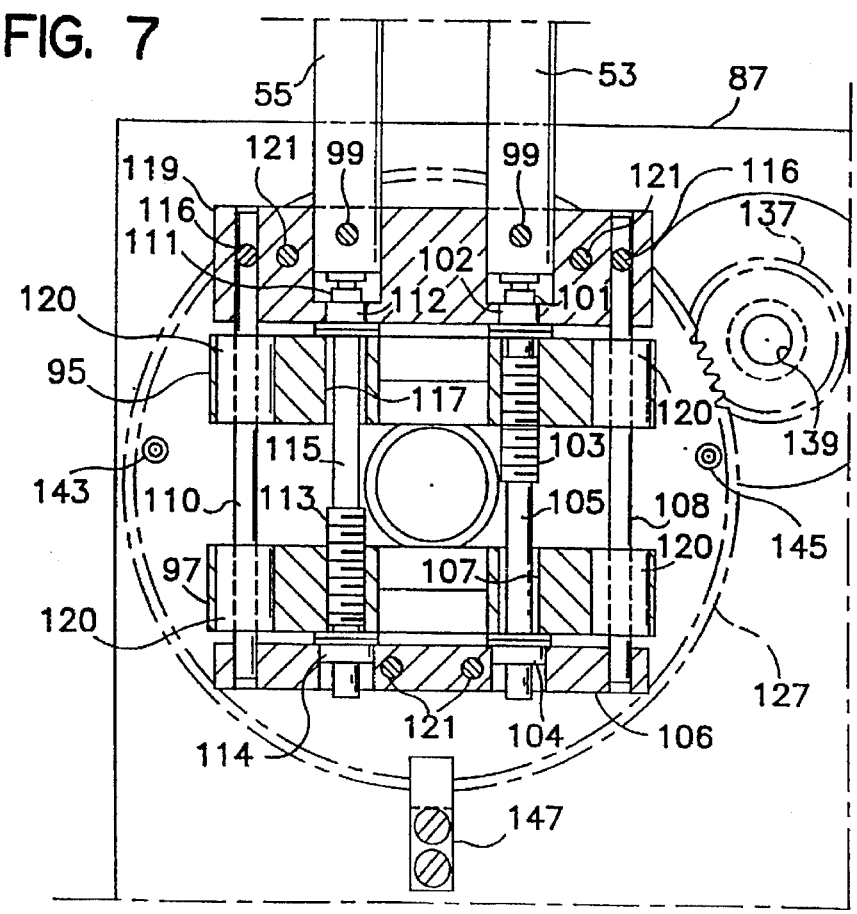
FIG. 7 is an enlarged, fragmentary, sectional view taken on the line 7,7 of FIG. 2 showing additional details of the drive mechanisms for the doors and the gear drive for the rotational position of the door assembly.

On the right hand side of the device 17 shown in FIG. 2, also known as the back or exit side, are a pair of door sections 95 and 97 respectively. FIG. 7 illustrates the manner in which upper door section 95 is driven by motor 53 and associated screw shaft 101, which shaft is in turn threaded into door section 95 by screw portion 103. The lower terminal end 105 of shaft 101 passes through clearance passage 107 in lower door section 97.

Motor mounting block 119 mounts the two motors 53 and 55 such that they are secured in bores in block 119 by means of set screws 99. The output shafts of the motors 53 and 55 are attached into the upper terminal ends of two screw shafts 101 and 111, respectively. The screw shafts 101 and 111 are mounted respectively in bearings 102 and 112 in the lower face of block 119. The lower terminal ends of screw shafts 101 and 111 are carried in bearings 104 and 114, respectively, in the lower mounting block 106. The upper door 95 threadedly engages with the threaded portion 103 of screw shaft 101 and is driven up or down by motor 53. The lower door section 97 threadedly engages with the threaded portion 113 of screw shaft 111 and is driven up or down by means of motor 55.

The two door sections 95 and 97 are stabilized for up and down motion using two guide rods 108 and 110 that extend between upper block 119 and the lower mounting block 106. The guide rods 108 and 110 are secured from movement by means of set screws 116 in the upper block 119. The two door sections 95 and 97 each have linear bearings 120 mounted on their outer ends to engage with the guide rods 108 and 110. The entire door assembly is mounted to the face of gear 127 by means of two screws 121 in the upper block 119 and two similar screws 121 in the lower mounting block 106.

Similarly, motor 55 and associated screw shaft 111 activates door section 97 by screw portion 113, such that the upper end 115 of shaft 111 has clearance for upper door section 95 through clearance passage 117.

Figure 3:
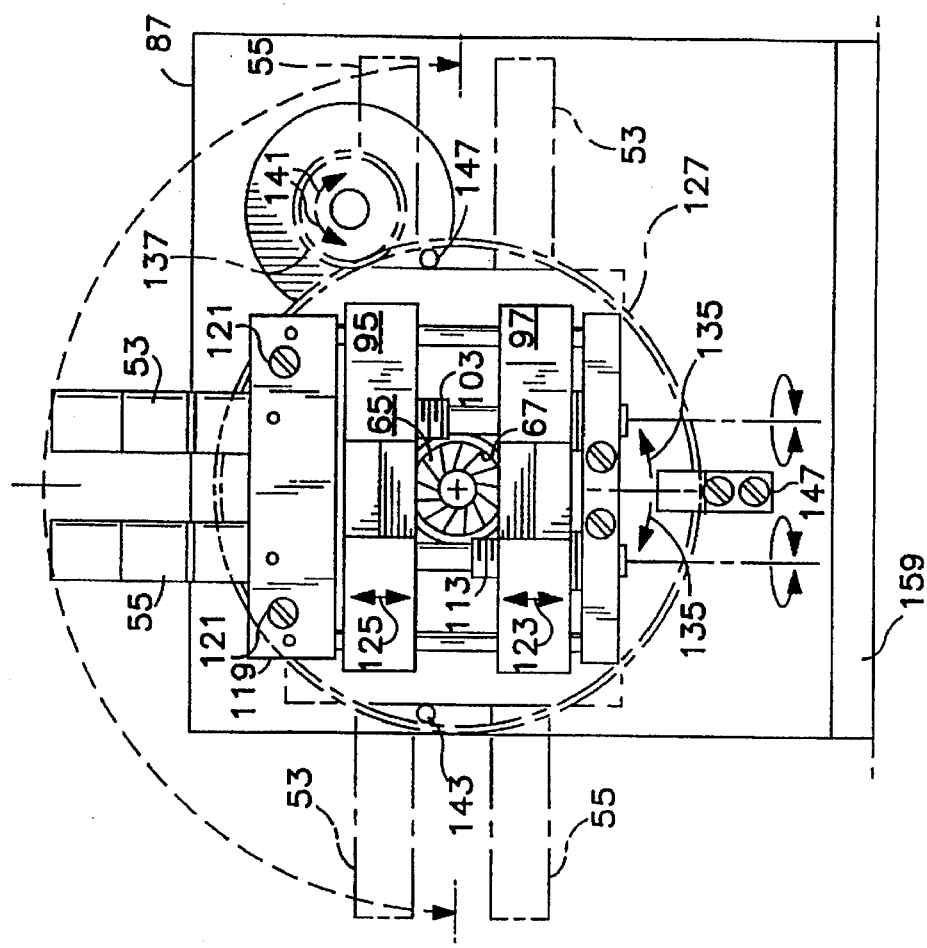
FIG. 3 is a rear or right hand elevational view of FIG. 2.

Motor mounting block 119 mounts motors 53 and 55 which in turn move door sections 95 and 97 respectively in the direction shown by arrows 123 and 125 in FIG. 3, for example, so as to restrict a laser beam passing through aperture 67 along axis 15. In the preferred embodiment shown herein, door section 95 is moved by motor 53 independent of whether or not door section 97 is moved by motor 55, and, of course, the reverse is true as well since both motors 53 and 55 are controlled and activated separately, depending upon the predetermined pattern. Thus one side or the other of the laser beam pulse may be larger or smaller than the other side as desired.

The entire door means including motors 53 and 55 are mounted on the motor mounting block 119, which block 119 is attached to a ring gear 127 by screws 121. Ring gear 127 is mounted on bearings 129, in turn mounted on flange 131. Flange 131 is attached by machine screws 133 to housing block 87. FIG. 3 illustrates the final axis of movement of the sculpturing device 17. Ring gear 127 moves in the direction of arrow 135 by spur gear 137 on drive shaft 139 of motor 37. Motor 37 rotates shaft 139 and spur gear 137 in the direction of arrow 141, rotating ring gear 127 about axis 15 by 180 degrees in both the clockwise and counterclockwise directions. Machine limit screws 143 and 145 limit travel to 180 degrees upon contact with limit stop 147 at the bottom of block housing 87. The device shown in FIG. 7 is limited to approximately but not less than 180 degrees of movement in each direction but other limits are possible as desired. It may be possible to travel a full 360 degrees with a different assembly.

It can now be seen that the sculpturing device 17 operates to restrict the laser beam traveling along laser beam axis 15 in four ways. First, the aperture 67, which can be enlarged or made smaller by iris diaphragm 69, circumferentially restricts the laser beam, such as for use in certain treatment such as myopia. Also, block sections 95 and 97 may be moved, independently in this embodiment, to further restrict the laser beam on one side or both sides as the predetermined pattern requires for second and third axes of restriction. Finally, the entire assembly may be rotated about the fourth axis, which is the laser beam axis, so that either door section 95 or 97, or both door sections, may restrict a different portion of the laser beam.

At every position, encoder 41 provides feedback to the controller as to the angular position of rotation about axis 15 in the direction of arrow 135. Similarly, encoder 49 provides feedback to the controller as to the angular position of iris diaphragm 69, and thus the size of aperture 67. Motors 53 and 55 are also provided internal encoders at the top thereof to provide feedback as to the position of door sections 95 and 97 by signaling the position of screw 103 in door section 95 and screw 113 in door section 971.

The sculpturing device 17 may be adjusted or serviced by removal of angularly shaped closure plate 149. Motors 37 and 41 are mounted to housing block 87 via machine screws 153. Screws 153 serve also to hold closure plate 149 in place as it rests on ledge 155, covering the mechanisms inside housing block 87, leaving a space between closure plate 149 and ring gear 75 as shown in FIG. 5. The shape of closure plate 149 is shown in FIG. 4 where the left side of closure plate 149 is in dash line in part to show the location of motors 37 and 41, among other things.

Figure 6:
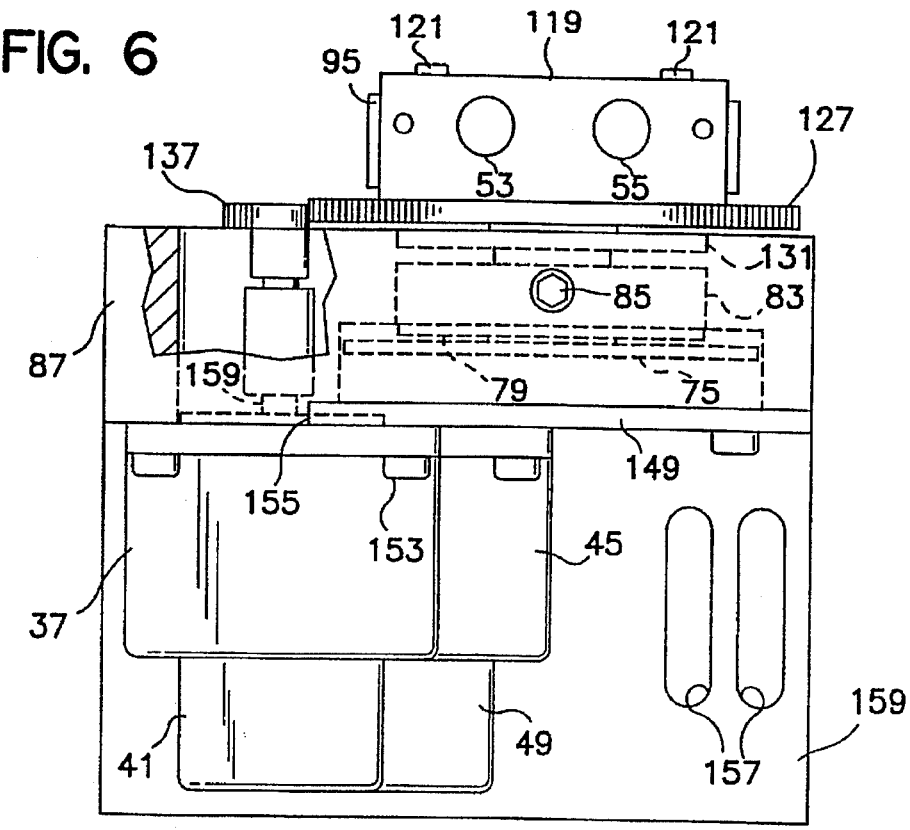
FIG. 6 is a plan view of FIG. 4 showing the drive mechanism for the angular disposition of the door and slot mechanism.

FIG. 6 is a top plan view illustrating the slots 157 in base plate 159 which permit precise mounting and location of the entire sculpturing device 17 on table 25 so that it may be properly oriented with respect to a laser 11 and the other components illustrated in FIG. 1.

Figure 8:
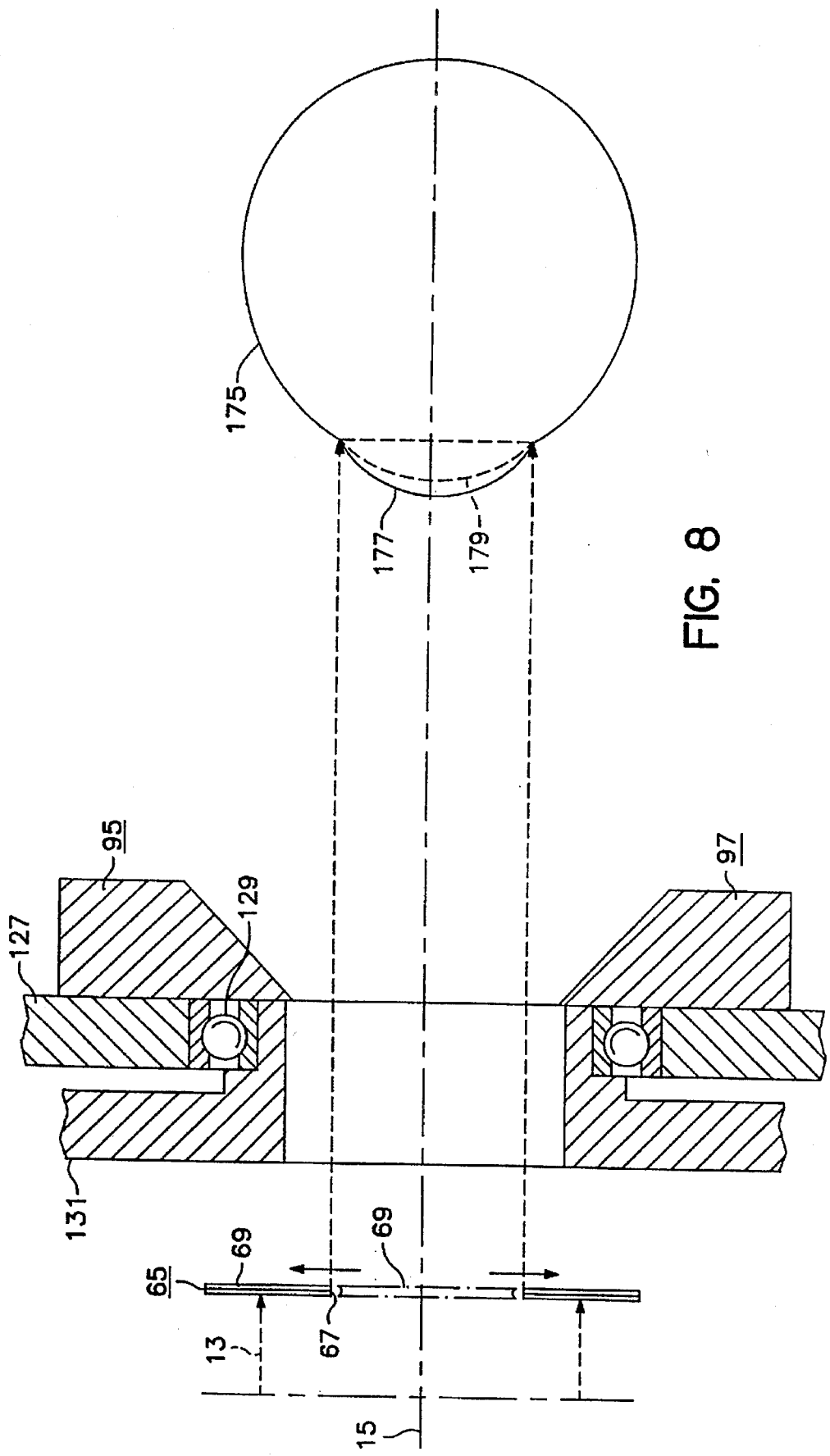
FIG. 8 is an enlarged, schematic view showing the general arrangement of the system of this invention for a surgical procedure on the eye to correct myopia.

As noted above, the present invention is admirably suited for use in eye surgery, and more particularly to treatment of the eye to correct astigmatism, myopia, or hyperopia. FIG. 8 illustrates the general arrangement of the device 17 as the laser beam 13 passes along axis 15, from left to right in the drawing, to first impact on diaphragm 69 of iris 65 and pass through that portion of the laser beam pulse that fits within aperture 67. The laser beam pulse is not restricted by door sections 95 and 97, shown in position next to ring gear 127, in turn supported as previously described on bearing 129 on flange 131. Eye 175 and cornea 177 are treated for myopia by the system in this configuration. The door sections 95 and 97 are fully open and the iris diaphragm 69 is fully closed. The laser is then pulsed one or more times at various predetermined settings as the iris is opened at predetermined increments. The dotted line 179 illustrates the flattened cornea after treatment.

Figure 9:
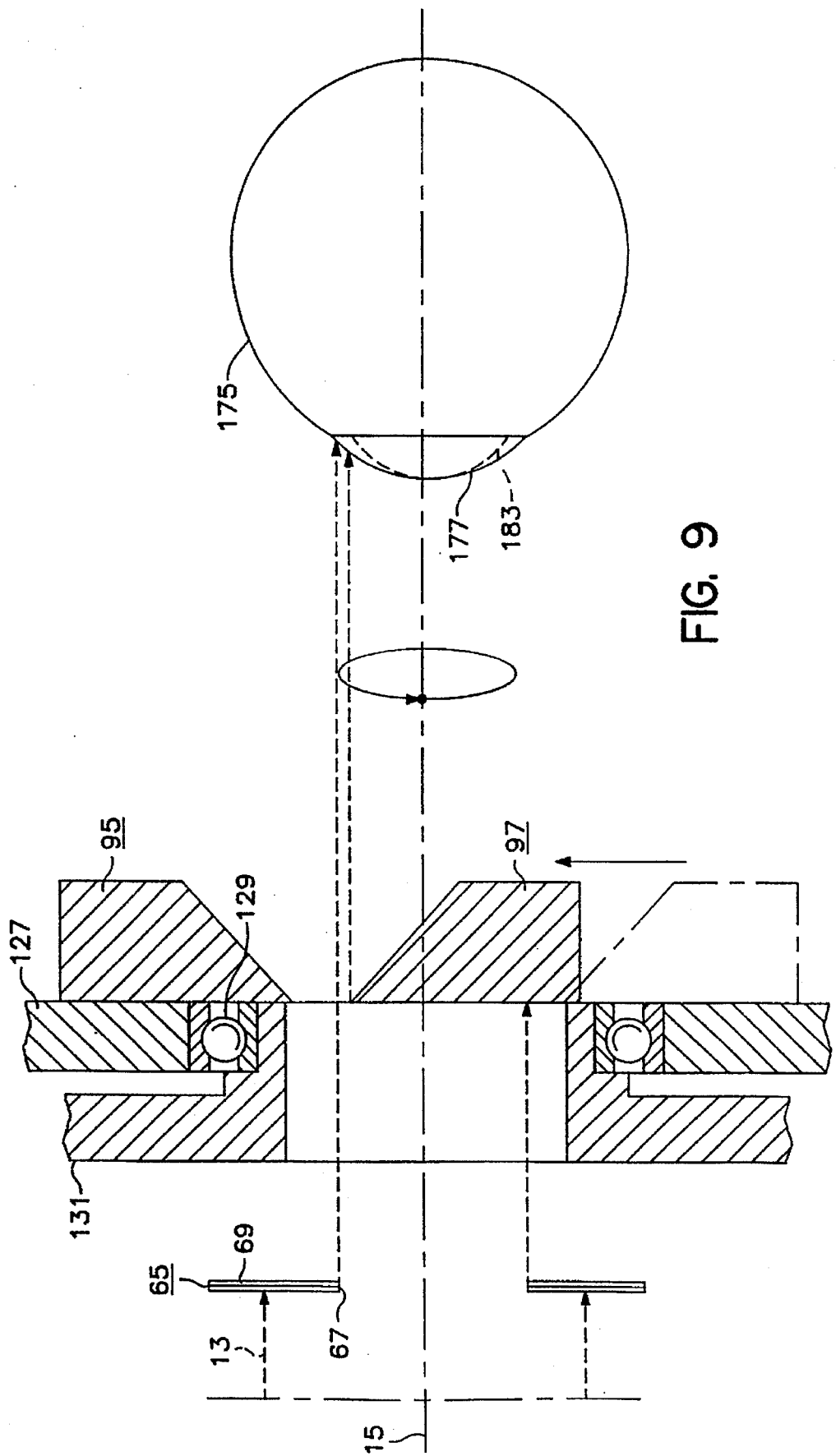
FIG. 9 is a view similar to FIG. 8 for a surgical procedure to correct hyperopia.

FIG. 9 illustrates a treatment for hyperopia in which the aperture 67 is open to a predetermined diameter. Upper door section 95 is open to its maximum spacing and lower door section 97 is raised to a chordial cutting position to exclude a large portion of the laser beam pulse. The door assembly is rotated at least once and preferably a plurality of times about axis 15 during laser pulsing. The procedure may also be repeated at varioius door settings to achieve the results 183 on the cornea 177 to produce hyperopic treatment.

FIG. 10 illustrates a treatment condition for astigmatism in which both upper door section 95 and lower door section 97 converge to a nearly closed position, as shown, to form a thin slit. In this procedure, the door assembly is not rotated other than initially when aligning the slit band 185 to the major axis 186 of the elliptically shaped cornea. Again, this procedure is repeated over varying predetermined increments of slit band width to achieve results 190 on cornea 177.

As will become apparent from reading the foregoing, the doors and iris of the sculpturing device of this invention may be manipulated to project a wide variety of laser beam patterns on a target such as, for example, the human eye. Such patterns include, by way of example and not of limitation, annuli of varying sizes, chords, eclipses, ovals and other curved shapes. Also, use of the door sections along the entire periphery of the beam, in sequential steps, permits projection of straight edged shapes such as rectangles and the like.

While particular embodiments of the present invention have been illustrated and described, it is not intended to limit the invention, except as defined by the following claims.

We claim:

1. A device for sculpturing a laser beam, said device being positionable between a laser source for directing a laser beam along a laser axis and a target for receiving said laser beam, comprising;

a housing;

an adjustable iris in said housing defining an aperture for adjustable movement about said axis;

door means in said housing for intersecting said laser beam by a predetermined amount comprising a pair of parallel, diametrically opposed door sections wherein said door means operates said pair of door sections independently so as to permit movement of one section without regard to movement of the other section; and control means connected to said housing for controlling said iris and said door means and the laser source to cooperatively direct a laser beam on a target in a predetermined pattern.

2. The device of claim 1, wherein said control means includes means for rotating said device about said laser axis.

3. The device of claim 2, wherein said means for rotating said device is adapted to rotate said device in both the clockwise and counterclockwise directions by at least 180 degrees.

4. The device of claim 1, wherein said target is a human eye.

5. The device of claim 4, wherein said target is a cornea of said human eye.

6. The device of claim 5, wherein said target is said cornea of said human eye, and said predetermined pattern is intended to shape said cornea.

7. The device of claim 6, wherein said target is said cornea of said human eye, and said predetermined pattern is intended to shape said cornea to treat a condition selected from astigmatism, myopia, hyperopia, and any combination thereof.

8. The device of claim 1, wherein said control means includes a computer.

9. The device of claim 8, wherein said computer is programmable to provide said predetermined pattern.

10. The device of claim 9, wherein said device is capable of automated operation.

11. A device for sculpturing a laser beam, said device being positionable between a laser source for directing a laser beam along a laser axis and a target for receiving said laser beam, comprising;

a housing;

an adjustable iris in said housing defining an aperture for adjustable movement about said axis;

at least one door means in said housing for intersecting said axis to limit a laser beam path by a predetermined amount, said door means including a pair of parallel, diametrically opposed door sections, one section being on each side of said axis, said door means operating said pair of door sections independently so as to permit movement of one section without regard to movement of the other section; and control means connected to said housing for controlling said iris and said door means and the laser source to cooperatively direct a laser beam on a target in a predetermined pattern.

12. The device of claim 11, wherein said control means includes means for rotating said device about said laser axis.

13. The device of claim 12, wherein said means for rotating said device is adapted to rotate said device in both the clockwise and counterclockwise directions by at least 180 degrees.

14. The device of claim 11, wherein said target is a human eye.

15. The device of claim 14, wherein said target is a cornea of said human eye.

16. The device of claim 15, wherein said target is said cornea of said human eye, and said predetermined pattern is intended to shape said cornea.

17. The device of claim 16, wherein said target is said cornea of said human eye, and said predetermined pattern is intended to shape said cornea to treat a condition selected from astigmatism, myopia, hyperopia, and any combination thereof.

18. The device of claim 11, wherein said control means includes a computer.

19. The device of claim 18, wherein said computer is programmable to provide said predetermined pattern.

20. The device of claim 19, wherein said device is capable of automated operation.

* * * * *